United States Patent [19]
Choksi et al.

[11] Patent Number: 6,050,263
[45] Date of Patent: Apr. 18, 2000

[54] ENDOTRACHEAL TUBE HOLDER

[75] Inventors: Pradip V. Choksi, Chatsworth;
Thomas R. Thornbury, Toluca Lake;
Arnold M. Heyman, Los Angeles;
Craig R. McCrary, Valencia, all of Calif.

[73] Assignee: Neotech Products, Inc., Chatsworth, Calif.

[21] Appl. No.: 09/100,996

[22] Filed: Jun. 22, 1998

[51] Int. Cl.$^7$ .............................. A61M 16/00; A62B 9/06
[52] U.S. Cl. ................. 128/207.14; 128/207.17; 128/DIG. 26; 604/174; 604/180; D24/128
[58] Field of Search ................ 128/200.26, 207.14, 128/207.15, 207.17, 207.18, DIG. 26; 604/174, 180; D24/128

[56] References Cited

U.S. PATENT DOCUMENTS

| | | | |
|---|---|---|---|
| 3,677,250 | 7/1972 | Thomas | 604/180 |
| 4,142,527 | 3/1979 | Garcia | 604/180 |
| 4,483,337 | 11/1984 | Clair | 128/207.17 |
| 4,683,882 | 8/1987 | Laird | 128/207.17 |
| 4,838,867 | 6/1989 | Kalt et al. | 604/180 |
| 4,867,154 | 9/1989 | Potter et al. | 128/207.17 |
| 5,009,227 | 4/1991 | Nieuwstad | 128/207.17 |
| 5,037,397 | 8/1991 | Kalt et al. | 604/174 |
| 5,267,967 | 12/1993 | Schneider | 604/174 |
| 5,308,339 | 5/1994 | Kalt et al. | 604/180 |
| 5,368,024 | 11/1994 | Jones | 128/207.17 |
| 5,383,451 | 1/1995 | DeIulio | |
| 5,626,565 | 5/1997 | Landis et al. | 604/174 |
| 5,743,885 | 4/1998 | Hoerby | 604/180 |
| 5,868,132 | 2/1999 | Winthrop et al. | 128/207.14 |
| 5,894,840 | 4/1999 | King | 128/200.26 |

OTHER PUBLICATIONS

"The Handy Bar: Endotracheal Tube Stabilizing Bar", Tony R. Van Deventer, MS, RRT, Neonatal Network, Oct., 1995, vol. 14, No. 7, pp. 65 & 66.

"Comparison of Two Methods for Securing the Endotracheal Tube in NeoNates", Teresa A. Volsko RRT and Robert L. Chatburn RRT, Respiratory Care, Mar., 1997, vol. 42, No. 3, pp. 288–291.

*Primary Examiner*—John G. Weiss
*Assistant Examiner*—Joe Weiss
*Attorney, Agent, or Firm*—William W. Haefliger

[57] ABSTRACT

An endotracheal tube holder, comprising, in combination an elongated arching support having opposite end portions adapted to be attached to a patient's left and right facial cheek zones which are preauricular areas of the cheeks, the support also having a mid portion adapted to be positioned in outwardly spaced relation to a patient's mouth; and a platform connected to the support to project outwardly away from the support mid portion, for attachment to and for supporting the endotracheal tube projecting from the patient's mouth.

18 Claims, 2 Drawing Sheets

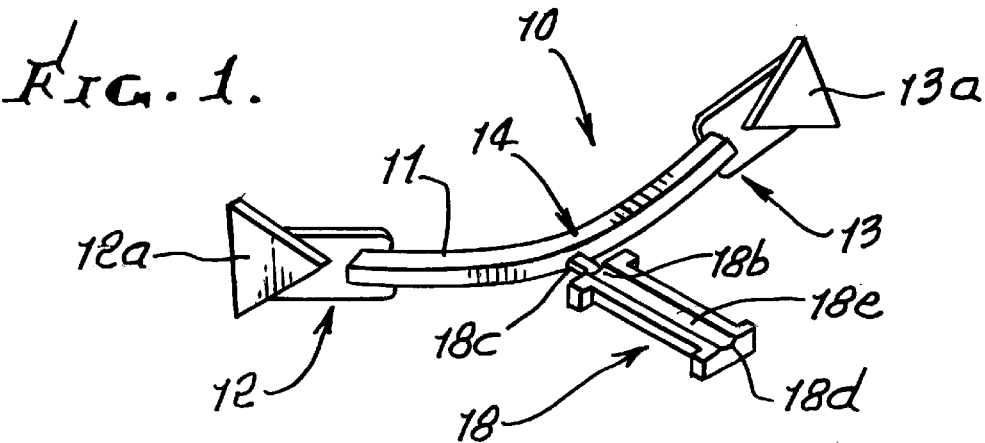
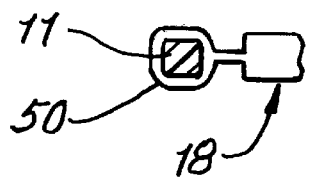
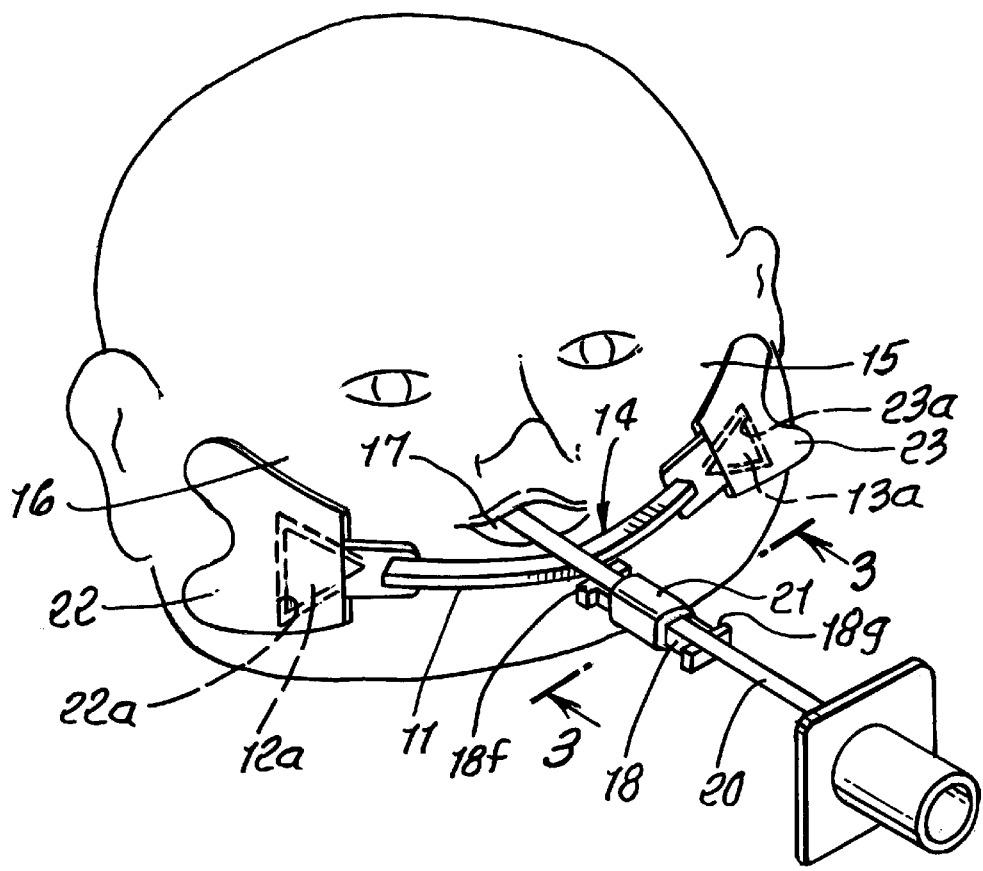

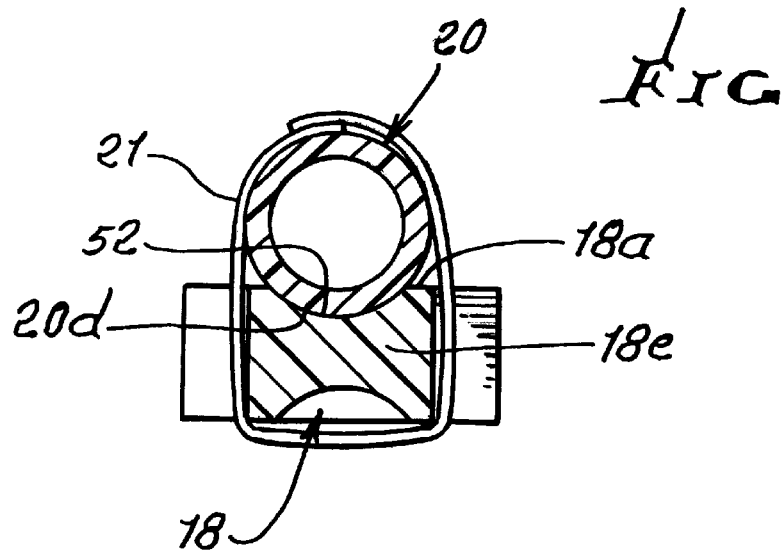
FIG. 3.
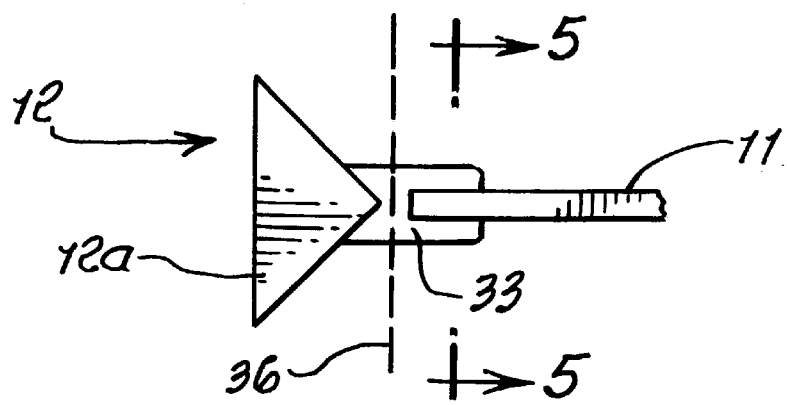
FIG. 4.
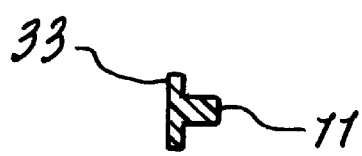
FIG. 5.
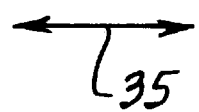

ENDOTRACHEAL TUBE HOLDER

BACKGROUND OF THE INVENTION

This invention relates generally to an endotracheal tube apparatus, and more particularly to stabilizing, supporting, securing, and positioning of the endotracheal tube (hereafter "ET tube"), after it has been inserted through the mouth into the trachea and the main stem bronchus.

Prior devices to support ET have suffered from disadvantages, such as bulkiness, instability, skin irritation, and difficulty in attachment to the user's face or neck. Prior devices have also proven to be generally unreliable. The significance of this unreliability is that the tube can be spontaneously extubated or removed if the holding device does not work properly. There is need for improved apparatus overcoming these and other disadvantages with prior ET tube support devices. Also, there is need for the unusually effective advantages in structure, function and results as are now provided by the present invention.

SUMMARY OF THE INVENTION

It is a major object of the invention to provide an improved ET tube holder, meeting the above needs. Basically the ET holder of the invention comprises:

a) an elongated arching support having opposite end portions to be attached to a patient's left and right facial zones, or preauricular area of the cheek, b) and a platform connected to the support to project outwardly away from the support mid portion, for attachment to and for supporting and stabilizing the endotracheal tube projecting from a patient's mouth or nose.

As will appear, the arching support and platform preferably consist of a one-piece molded plastic unit, the arching support having narrowed width providing yieldably resilient bending flexibility. The platform is typically connected as by a molded hinge to a portion of the arching support.

It is another object to provide a platform as referred to which has opposite ends and a narrowed width medial region between such opposite ends, about which tape may be wrapped about the platform and the tube, and confined between the platform opposite ends.

Yet another object is to provide the arching support to have opposite end portions including attachment tabs having hinged connection to the arching support, thereby enhancing support flexibility during use, as when the user's cheek regions are moved relative to one another. Attachment pads are preferably attached to the arching support end portions, the pads adhering to the infant's left and right facial cheek zones. Also the pads preferably provide hydrocolloid or hydrogel surfaces to contact the cheek zones, to preserve skin integrity. In this regard, the pads preferably lock to the end portions of the arched support, those end portions typically having delta configuration, to enhance the lock-in to the pads.

Yet another object is to provide the arching support to consist of a molded plastic strand with cross-sectional thickness along its length less than about ⅛ inch.

The method of use of the invention comprises the steps:

c) attaching the endotracheal tube to the platform to extend crosswise of the arching support, as it projects from the mouth of a patient, and d) providing attachment pads in association with the support opposite end portions, and e) attaching those pads to facial zones of a patient. The step c) attaching typically includes removably connecting the tube to the platform. An additional step includes removing the connection, while allowing the platform to deflect relative to the support.

Unusual advantages of the invention include provision for stabilizing the arched support, hinging of the platform to the support allowing for rapid tube removal, and also tube replacement and re-taping, while the apparatus remains firmly connected to the patient's face; provision of a tube stabilizing platform to prevent tube buckling; provision of apparatus allowing easy suctioning and cleaning of the oral cavity, provision for hydrocolloid or hydrogel attachment to the patient's skin surface, to preserve skin integrity; elimination of need for use of connection tape near the patient's nose or mouth; and the saving of time, by standardization in use and application.

These and other objects and advantages of the invention, as well as the details of an illustrative embodiment, will be more fully understood from the following specification and drawings, in which:

DRAWING DESCRIPTION

FIG. 1 is a perspective view of endotracheal tube holder apparatus embodying the invention; and FIG. 1a is a section taken through a movable connection between a platform and a support bar;

FIG. 2 is a view like FIG. 1, but showing an endotracheal tube in use, and supported by the holder apparatus;

FIG. 3 is an enlarged section taken on lines 3—3 of FIG. 2;

FIG. 4 is an enlarged elevational view of an end portion of the holder; and

FIG. 5 is a section taken on lines 5—5 of FIG. 4.

DETAILED DESCRIPTION

In the preferred embodiment shown in FIG. 1, the ET holder 10 includes an elongated arching narrow support or bar 11, having like opposite end portions 12 and 13 adapted to be attached to a patient's left and right facial cheek zones, such as preauricular areas on the cheeks, seen for example at 15 and 16 in FIG. 2. The arching support also has a mid or medial portion 14 adapted to be positioned in outwardly spaced relation to a patient's mouth 17. The patient is typically a newborn infant. A platform 18 is shown as connected to and carried by the support 11, to project outwardly away from the support mid or crest portion 14, for attachment to and for supporting the endotracheal tube 20 indicated as projecting from the patient's mouth 17. FIG. 3 shows tube 20 supported on the top surface 18a of the platform.

The arching support and platform preferably consist of a one-piece, molded plastic unit, the arching support having narrowed width providing yieldably resilient bending flexibility. As shown, the platform has one end 18b connected to a crest defined by said mid portion of said arching support. Platform end 18b is shown as having hinged connection at 18c to the arching support. FIGS. 1 and 3 show the location and reduced thickness of the plastic molded hinge, which allows limited side to side deflection of the platform, to accommodate the positioning of the ET tube 20.

The platform has opposite ends 18b and 18d, and a narrowed width medial region 18e between those ends, and about which tape 21 may be wrapped, about the platform medial region and the ET tube, as seen in FIGS. 2 and 3. Accordingly, the wrapped tape is confined between the relatively greater width platform opposite ends, to prevent tape slippage off the platform. Therefore the ET tube is endwise confined by the platform, because tape 21 is endwise confined between platform shoulders 18f and 18g.

The arched support opposite end portions 12 and 13 include integral attachment tabs 12a and 13a, that have hinged connection to the arching support. Therefore, the arched support can flex, at its opposite ends, relative to the tabs 12a and 13a after those tabs are attached to the patient's facial cheek region. See the flex direction indicated by arrows 35 in FIG. 5, i.e. toward and away from the wearer's face. The hinging axis is seen at 36 in FIG. 4. Such capacity for flexing, without detachment from the cheeks, is desirable, as during tape attachment to, or detachment from, the platform and EDT tube.

Tabs 12a and 13a may have irregular peripheral configuration, as for example delta shape, to enhance or secure their locking to and within pockets 22a and 23a formed by larger, thin pads 22 and 23. These pads also consist of molded plastic material, and may have attachment to the patient's facial cheek regions, at selected locations. Hydrocolloid material may be on the pad surfaces adherent to the tender cheek skin, for minimizing irritation.

Molded hinges 33 of reduced width, connect the tabs 12a and 13a to the arching support strand ends, as seen for example, in FIG. 4.

In use, the tube 20 may be tape connected to the platform after its insertion into the trachea; and the pads 22 and 23 being adhered to the patient's cheeks at selected locations such that the platform is correctly positioned frontwardly or outwardly spaced from the patient's mouth. Such positioning is facilitated by the enabled hinging of elements, as referred to.

The platform 18 may have movable connection to the support bar 11, as for example indicated by the FIG. 1a slide ring 50 extending about the bar 11, that ring being integral with the platform.

FIG. 3 shows a concave recess at 52 on the platform 18 upper surface, to receive and position a side portion 20d of the tube 20. Other means on the platform to position the tube 20 may be provided.

Finally, the support bar and platform and also the tube 20, may have coloration to indicate size, and such coloration may be different for different elements.

The apparatus as described may be considered as one preferred form of the ET holding apparatus. Other equivalent forms may be provided.

We claim:

1. An endotracheal tube holder, comprising:
   a) an elongated arching support having opposite end portions adapted to be attached to a patient's left and right facial cheek zones which are preauricular areas of the cheeks, the support also having a mid portion adapted to be positioned in outwardly spaced relation to a patient's mouth,
   b) and a platform connected to the support to project outwardly away from said support mid portion, and adapted for attachment to and for supporting an endotracheal tube when projecting from the patient's mouth,
   c) and there being attachment tabs having hinged connections to said arching support.

2. The tube holder of claim 1 wherein said arching support and platform consist of a one-piece, molded, plastic unit, the arching support having narrowed width providing yieldably resilient bending flexibility.

3. The tube holder of claim 1 wherein said platform is connected to a crest defined by said mid portion of said arching support.

4. The tube holder of claim 1 wherein said platform has hinged connection to said arching support.

5. The tube holder of claim 1 wherein said platform has opposite ends and a narrowed width medial region between said opposite ends about which tape may be wrapped about the platform and said tube, and confined between said platform opposite ends.

6. The tube holder of claim 1 wherein said arching support consists of a molded plastic elongated support with cross-sectional thickness along its length less than about ⅛ inch.

7. The tube holder of claim 1 wherein the platform has movable connection to the support to be movable thereal-ong.

8. The tube holder of claim 1 wherein the platform has a concave recess adapted to receive a side portion of an endotracheal tube.

9. The tube holder of claim 1 wherein the platform has a means for positioning an endotracheal tube.

10. The tube holder of claim 1 wherein the support and platform have coloration.

11. The tube holder of claim 1 wherein said hinged connections are defined by thin molded plastic hinges.

12. The tube holder of claim 11 including attachment pads locking to said tabs, the pads adherent to said infant's left and right facial cheek zones.

13. The tube holder of claim 12 wherein said pads have hydrocolloid or hydrogel surfaces to contact said cheek zones.

14. The tube holder of claim 12 wherein said arching support end tabs have locked attachment to said pads, the pads having hinged attachment to the arching support to allow flexing in directions toward and away from said facial cheek zones.

15. The tube holder of claim 14 wherein said arching support end tabs have tapered configuration.

16. The method of using an endotracheal tube holder that comprises:
   a) an elongated arching support having opposite end portions adapted to be attached to a patient's left and right facial cheek zones, the support also having a mid portion adapted to be positioned in outwardly spaced relation to a patient's mouth,
   b) and a platform connected to the support to project outwardly away from said support mid portion, for attachment to and adapted for supporting an endotracheal tube when projecting from the patient's mouth, said method including the steps:
   c) attaching an endotracheal tube to said platform to extend crosswise of the arching support, for reception in the mouth of a patient, and
   d) providing attachment pads and hinges in hinging association with the support opposite end portions, and
   e) attaching said pads to facial zones of a patient.

17. The method of claim 16 wherein said step c) attaching includes removably taping said tube to said platform.

18. The method of claim 14 including removing said tape, while allowing the platform to hingedly deflect relative to the support.

* * * * *